(12) United States Patent
Shine et al.

(10) Patent No.: US 6,699,680 B1
(45) Date of Patent: Mar. 2, 2004

(54) METHOD OF DETERMINING A NUMBER OF PLATELETS

(76) Inventors: Ian Basil Shine, 444 Central Park West, New York, NY (US) 10025; Thomas Adam Shine, Apt. #3, 220 Lawrence St., New Haven, CT (US) 06511

( * ) Notice: Subject to any disclaimer, the term of this patent is extended or adjusted under 35 U.S.C. 154(b) by 0 days.

(21) Appl. No.: 09/623,186
(22) PCT Filed: Dec. 24, 1999
(86) PCT No.: PCT/GB99/04428

§ 371 (c)(1), (2), (4) Date: Aug. 29, 2000

(87) PCT Pub. No.: WO00/39559

PCT Pub. Date: Jul. 6, 2000

(30) Foreign Application Priority Data

Dec. 29, 1998 (GB) ............................................. 9828765
May 4, 1999 (GB) ............................................. 9910266
May 4, 1999 (GB) ............................................. 9910267

(51) Int. Cl.$^7$ ................................................ C12Q 1/56
(52) U.S. Cl. ......................... 435/13; 356/337; 422/73
(58) Field of Search ............................. 435/13; 356/39, 356/337; 422/73; 436/8, 10, 17, 18

(56) References Cited

U.S. PATENT DOCUMENTS

| | | | |
|---|---|---|---|
| 3,851,246 A | 11/1974 | Curby et al. ............. | 324/71 CP |
| 4,298,836 A | 11/1981 | Groves et al. ........... | 324/71 CP |
| 4,375,615 A * | 3/1983 | Haynes ...................... | 324/71.4 |
| 4,521,729 A | 6/1985 | Keisewetter et al. ....... | 324/71.1 |
| 4,791,355 A | 12/1988 | Coulter et al. ............ | 324/71.1 |
| 4,810,963 A | 3/1989 | Blake-Coleman et al. .. | 324/204 |
| 4,876,504 A | 10/1989 | Blake et al. ................ | 324/204 |
| 5,006,460 A | 4/1991 | Thomas, Jr. et al. ........... | 435/6 |
| 5,464,752 A | 11/1995 | Kortright et al. .......... | 435/7.24 |
| 5,532,139 A | 7/1996 | Miller .......................... | 435/29 |
| 5,700,632 A | 12/1997 | Critser et al. .................. | 435/2 |
| 5,856,665 A | 1/1999 | Price et al. ................. | 250/205 |
| 6,218,190 B1 * | 4/2001 | Shine et al. .................. | 436/63 |

FOREIGN PATENT DOCUMENTS

| | | |
|---|---|---|
| CA | 988319 | 5/1976 |
| EP | 0010526 | 4/1980 |
| WO | WO 97/24598 | 6/1997 |
| WO | WO 97/24529 * | 7/1997 |

OTHER PUBLICATIONS

Bessman J. Evaluation of Automated Whole Blood Platelet Counts and Particle Sizing. American J of Pathology Aug. 1980. 74(2)157–162.*

Thorsen T. A Method For Production of N2 Microbubbles in Platelet Rich Plasma . . . Undersea Biomedical Research 13(3)271–287, 1986.

Latimer, Paul Applied Optics, vol. 14, No. 10, Oct. 1975, pp. 2324–2326.

Bryant et al. Archives of Biochemistry and Biophysics, vol. 135, Dec. 1969, pp. 109–117.

Eskelinen et al. Cation permeability and mechanical properties of the erythrocyte membrane under the influence of lysophosphatidylcholine (LPC) in isotonic and hypotonic media. Acta Physiol. Scand. 122 (4), pp. 527–534. (Dec. 1984).

Richieri et al. Measurement of biophysical properties of red blood cells by resistive pulse spectroscopy: volume, shape, surface area, and deformability. J. Biochem. And Biophys. Methods 11, pp. 117–131. (1985).

Born, G.V.B. Nature, vol. 194, Jun. 1962, pp. 927–929.

Remuzzi et al. Biorheology, vol. 21, No. 4, Dec. 1984, pp. 617–630.

Latimer, Paul Biophysical Journal vol. 27, Jul. 1979, pp. 117–126.

Thorsen et al. A method for production of $N_2$ microbubbles in platelet–rich plasma in an aggregometer–like apparatus, and effect on the platelet density in vitro.

Bateman, J.B. Journal of Colloid and Interface Science vol. 27, No. 3, Jul. 1968.

Linderkamp et al. Geometric, osmotic, and membrane mechanical properties of density–separated human red cell. Blood 59 (6), pp. 1121–1127. (Jun. 1992).

Kieler et al., Histochemistry 92: 141–148 (Feb. 1989).

McLean et al. Life Sciences vol. 6, Sep. 1967, pp. 1983–1986.

* cited by examiner

*Primary Examiner*—Ralph Gitomer
(74) *Attorney, Agent, or Firm*—Perman & Green, LLP

(57) ABSTRACT

A method of determining a measure of the number of platelets in a cell suspension containing platelets. The number of small particles in the suspension is counted. The suspension is agitated in the presence of a gas. The number of small particles in the suspension after agitation is counted. The two counts are compared to obtain a measure of the number of platelets.

7 Claims, 5 Drawing Sheets

A

B

C

D

E

F

A

B

C

D

E

F

A

B

C

D

E

A

B

C

D

METHOD OF DETERMINING A NUMBER OF PLATELETS

FIELD OF THE INVENTION

The present invention relates to a method of analysing a sample of free cells, in particular blood cells.

BACKGROUND TO THE INVENTION

Automated block analysers which count and size blood cells, represent a huge advance in the field of chemical medicine, but retain some drawbacks. They are inherently incapable of differentiating like sized particles. While the automated count may be correct in terms of the total number of particles, traditional methods do not count small red cells, parasites or bits of cells as platelets. Anyone in need of good quality platelet counts is well advised to travel to Africa or Asia which, having few automated blood analysers, provide better quality complete blood counts because manual methods of counting avoid several errors which are common concomitants of automated sizing and counting instruments. Errors in counting platelets have serious consequences for the patient as they may result in unnecessary tests, inappropriate treatment, or mis-diagnosis. The known causes of spurious low platelet counts are EDTA dependent clumping, cold platelet agglutination, platelet satellitism and the presence of like sized particles which are not platelets.

All haematology texts, laboratories and manufacturers have been aware of the inaccuracies of automated platelet counts for many years and advise a manual inspection of a blood film for every patient with an abnormal platelet count, which is the practice in most haematology laboratories. Currently manufacturers are attempting to reduce errors by detecting light refraction (since platelets are more refractile) or by detecting stains applied to platelets before they reach the sensor. The practice of manual verification whenever the platelet measurements fall outside the normal range is comforting to the patient but expensive for the laboratories. However, hitherto, there was no method of alerting labs of the need for manual verification for patients with high platelet counts that erroneously fell inside the normal range. Thus automated platelet counts are of limited value when platelet counts are low, they are of uncertain value when the counts are normal, and are not entirely secure when the counts are elevated (thrombocytosis).

As will be discussed below, the applicants have discovered that there are other small particles, cell fragments, which are also not detected and properly distinguished by existing automated blood cell analyzers. The importance of cell friability or the generation of cell fragments has hitherto not been recognised.

SUMMARY OF THE INVENTION

According to one aspect of the present invention, there is provided a method of determining a measure of the number of platelets in a cell suspension containing platelets, the method comprising the steps of: counting the number of small particles in the suspension; agitating the suspension in the presence of a gas; counting the number of small particles in the suspension after agitation; and comparing the two counts to obtain a measure of the number of platelets.

The method of the invention differentiates platelets from other small particles exploiting a simple physiological property and removes spuriously low automated platelet counts. The accurate measurement of platelet number and function is of great consequence to a patient's health. Aside from bleeding to death from thrombocytopenia (insufficient platelets), platelets are risk components of strokes, heart attacks, and inflammation, and are important elements in the growth of epithelial malignancies and metastases.

All red cells are very sensitive to osmotic stress, and most cells are sensitive to mechanical stress. It has been found that platelets are relatively insensitive to mechanical and osmotic stress except when exposed to contact with air. Platelet suspensions alter their properties upon exposure to air, or its component gases to a greater extent if they are simultaneously stressed. By carefully controlling the handling of platelets before and during testing, by eliminating or regulating a suspension's exposure to air, more accurate platelet counts can be obtained. By intentionally exposing platelets to air while subjecting them to stress any induced change in the platelet population can be recorded. Because existing methods ignore the effect of air, they are inducing errors in their platelet counts.

The methods described in WO 97/24598, WO 97/24599 and WO 97/24601 provide a way to measure the size, shape, and number of particles while the particles are simultaneously exposed to a variety of osmotic gradients. However, further information may be derived from this test by combining it with the present invention. For example, by testing a whole blood suspension under osmotic stress, and comparing the results to the same sample after mechanical agitation in the presence of air, the components of the sample population which are altered by mechanical agitation in the presence of air can be determined. Furthermore, the types and proportion of each type can be revealed in a single procedure. Thus, red cells, white cells, micro-spherocytes, and bacteria are uninfluenced by mechanical agitation in the presence of air whereas platelets alone disappear. The advantage of this method in that in addition to explaining a way to differentiate and count platelets, it offers existing instruments a very simple method of increasing the accuracy of their counts.

In this application we also disclose a method of measuring cell friability since mechanical stress induces fragmentation in those cells. When cells are counted in cell counters, neither lysis nor fragmentation nor ghosts are induced. When cells are subjected to osmotic stress they lyse and ghost or fragment or both. The addition of mechanical agitation enhances the effect and the addition of air into the agitated suspension further intensifies the effect. Thus, in order to differentiate between cell fragments and platelets, it has been found to be preferable to compare the count of small particles before and after agitation in the presence of air against osomolality. This process of inducing the nature of these small particles can be likened to the identification of an unknown fluid by raising its temperature; if it boils at 78° C. it is ethyl alcohol, if it boils at 100° C. it is water and at 357° C. it is mercury.

In order to provide quantative measures from the present invention, it is preferable to monitor at least one of the following: A) the air quantity in contact with the suspension, B) the intensity of agitation and C) the duration of agitation, and to relate this measured value to the difference between the two counts.

The small particles counted in the method of the invention include platelets, bacteria, cell fragments, and microspherocytes, which typically have a volume of 7–10 femtoliters.

According to another aspect of the present invention, a method of analysing a sample of free cells in vitro comprises applying a known or identifiable quantity of stress to the sample, measuring the sample before and after the application of stress to provide at least one reading from which quantitative information relating to the number of cell fragments in the sample caused by the applied stress can be determined, and relating this reading to the quantity of stress to provide an indication of cell friability.

When red cells die, they lose their contents, a process termed lysis. They are then transformed into either ghost cells or fragments depending, in part, on the cell's membrane properties, and in part on the provocation. Hitherto, this mechanism has been little recognised or understood.

The present invention is based on the realisation that if cells, such as blood cells, and in particular red cells, are stressed in vitro the relationship between the applied stress and fragmentation to the sample is characteristic for normal samples and for many diseases. Since some cells (platelets) produce no detectable fragments and some (red cells) produce a large number this method also provides a way of distinguishing between certain cell types.

Existing automated particle analysers are of limited use in detecting fragments as they cannot identify fragmentation that was cleared in vivo by increased phagocytosis, and when fragments were not phagocytosed, it cannot easily differentiate them from platelets, apoptotic bodies, microspherocytes, parasites and noise. There are many patients whose cells are fragmenting yet no fragments are detected by existing methods because the body's physiological clearing mechanism removes fragments as fast as they are produced.

The method of the present invention has been found to be remarkably good at identifying certain blood abnormalities because it detects patients whose cells fragment when stressed. Because applied stress affects red blood cell fragments and platelets differently, it is possible to distinguish between the two. This has not been possible in the prior art particle counters because platelets and red blood cells fragments are usually not measured individually. In addition, as a sample can be tested before, during and after a stress has been applied, the induced effect provides an indication of the physiological fragmentation potential and the physiological removal rate.

The invention can be used to identify the age of population of cells since old cells fragment readily whereas new ones do not fragment readily. This may be useful in blood-banking, for instance, to destroy selectively a particular population of cells using a particular range of stresses, thereby prolonging the life of the unit by culling the old cells.

The applied stress can be mechanical, chemical, thermal, sonic, light, electric, electromagnetic, or any other means which induces membrane stress including in vitro aging of the cell sample. Preferably, the cells are subjected to an osmotic gradient. They may also be agitated by a stirring bar, by shaking vigorously, or by any other type of stress. More than one stress mechanism can be used at the same time if necessary. Indeed this may be beneficial in identifying certain abnormalities.

It is, however, preferable to apply a known stress, and more preferable to apply a range of stresses, which may be decreasing or haphazard, but is preferably increasing, so as to obtain a plot of the relationship between the number of red blood cell fragments and the applied stress. This range of stresses can be applied by varying duration and/or intensity, for example, by virtue of mechanically agitating the sample increasingly vigorously, by mechanically agitating the sample at a constant rate over an increasing period of time, by diluting the sample with a solution which gradually decreases in osmolality, or by any combination of these mechanisms. The latter approach can be carried out using the apparatus disclosed in WO 97/24529, which generates an osmolality gradient.

Characteristics providing the quantative information relating to the number of cell fragments include the detection of the fragments themselves, an alteration in the frequency distributions of multiple cell populations, an increase in the total particle count, a change in the concentration of intact cells, a change in the concentration of membrane or cytosolic parts, such as haemoglobin release, or other such phenomena related to induced cell fragmentation.

The step of counting the number of small particles is preferably done using a conventional commercially available particle counter, or using the apparatus disclosed in WO 97/24600. In both cases, the blood sample is caused to flow through a sensor, typically an aperture, where its size is detected optically, acoustically, thermally, electronically or by other means. In an impedance sensor, the response of the electrical field to the passage of the cells is recorded as a series of voltage pulses, the amplitude of each pulse being a function of cell fragment size and frequency.

In the absence of applied stress, existing instruments are unable to distinguish between platelets and, for instance, red cell fragments. As each different cell type has its own biochemical individuality and its own sensitivity to fragmentation, it is possible to use its response as an identifying property, identifying the cell type, sensitivity and pathology. For instance, platelets which are-similar in size to fragments, are differentiated from fragments as they respond differently when stressed. The differentiation and identification of fragments, platelets, ghost cells and other cell parts may be facilitated by using stains and dyes which selectively dye cell lines, or bond onto specific cell parts, for instance the inside and outside of the cell membrane or only stain the platelets. When a stress has been applied to a blood sample, as for example, in WO 97/24598, WO 97/24599 and WO 97/24601, it was performed to obtain accurate volume and other cell measurements by forcing cells to a known shape. The method disclosed herein induces cells to fragment and measures the result of fragmentation. This may be enhanced by, for instance, eliminating all particles except for the fragments of interest by setting the upper and lower threshold voltages to the size range of fragments, by facilitating fragmentation by applying heparin or other suitable chemicals in the chemical preparation of the sample and/or by allowing sufficient time for fragmentation to proceed. The induction, detection and quantification of fragments enhances the measures produced by WO 97/24598, WO 97/24599 and WO 97/24601 and other measures which may be altered by induced or existing fragments.

When using an electrical particle counter, the thresholds should be set low enough to detect cells down to a volume of almost 0 femtoliters. A threshold voltage of 0.08 mV has been found to work well with the existing apparatus. Other populations of particles may be eliminated electronically, digitally, mechanically, or by other means.

The commercially available particle counters and the device disclosed in WO 97/24600 can be used to provide adequate readings for the present invention. However, more accurate readings can be obtained if the size of the aperture in either device is reduced so that the ratio of the cross section of the aperture to the mean cross section of the red blood cell fragments or platelets is substantially 4:1.

In conventional blood cell analysis techniques, it is usual to treat the sample with an anticoagulant, such as EDTA, prior to analysis. However, it tends to inhibit fragmentation. It has therefore been found preferable not to treat the sample with an anticoagulant or to use an anticoagulant which does not inhibit or promote fragmentation, such as heparin.

BRIEF DESCRIPTION OF THE DRAWINGS

Examples of the present invention will now be described in detail with reference to the accompanying drawings, in which.

DETAILED DESCRIPTION

Examples of results obtained using the method according to the present invention, will now be described with reference to FIGS. 1 to 5 of the accompanying drawings, which are frequency distributions indicating the profile of the cell size measurement against increasing stress for a sample of cells tested using the apparatus disclosed in WO 97/24529 and the electrode disclosed in WO 97/24600.

Such frequency distributions have previously been used, for example in WO 97/24598, WO 97/24599, and WO 97/24601, for example to provide indications of the cell permeability, osmolality and cell shape respectively of normal unfragmented red blood cells.

The samples tested were treated with heparin, mechanically agitated by stirring or shaking in air, then subjected to an osmotic gradient using the apparatus disclosed in WO 97/24529.

Figure 1:
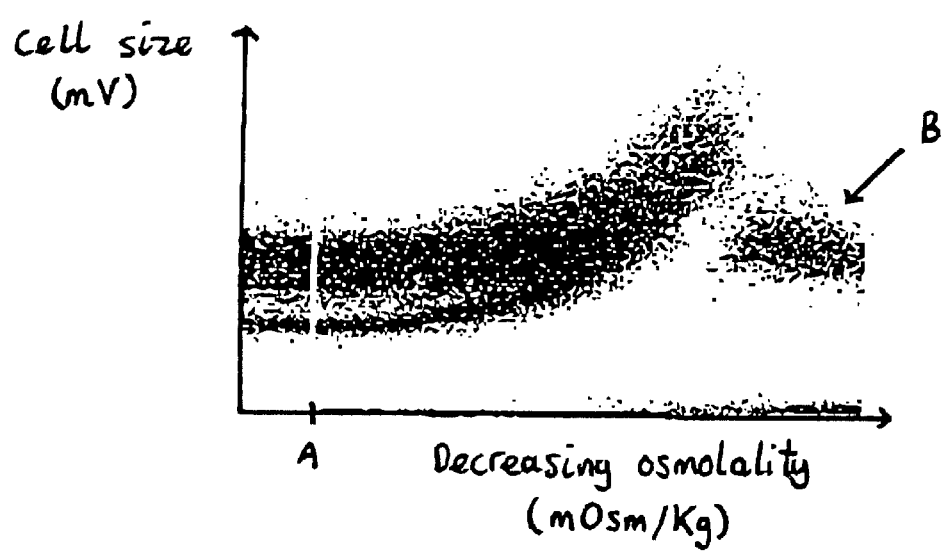
FIGS. 1 to 5 are frequency distributions indicating the profile of cell size measurement against increasing osmotic and mechanical stress for a number of cell samples.
Figure 2:
Figure 2:
Figure 2:
Figure 2:
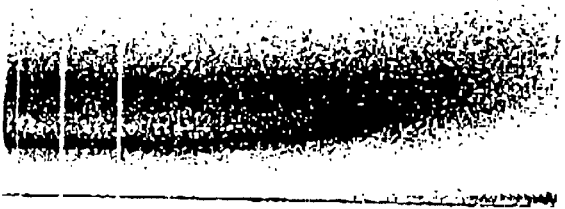
Figure 2:
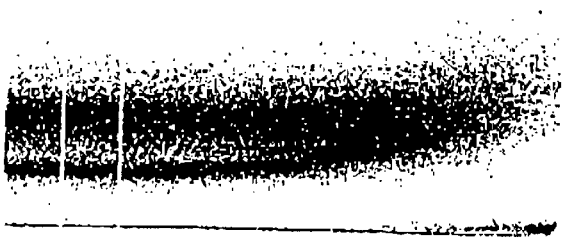
Figure 2:
Figure 3:
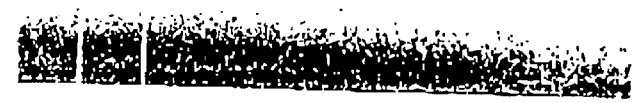
Figure 3:
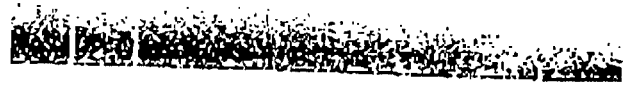
Figure 3:
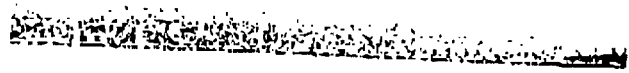
Figure 3:
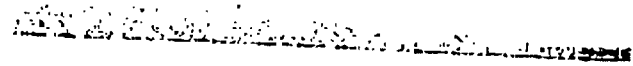
Figure 3:
Figure 3:
Figure 4:
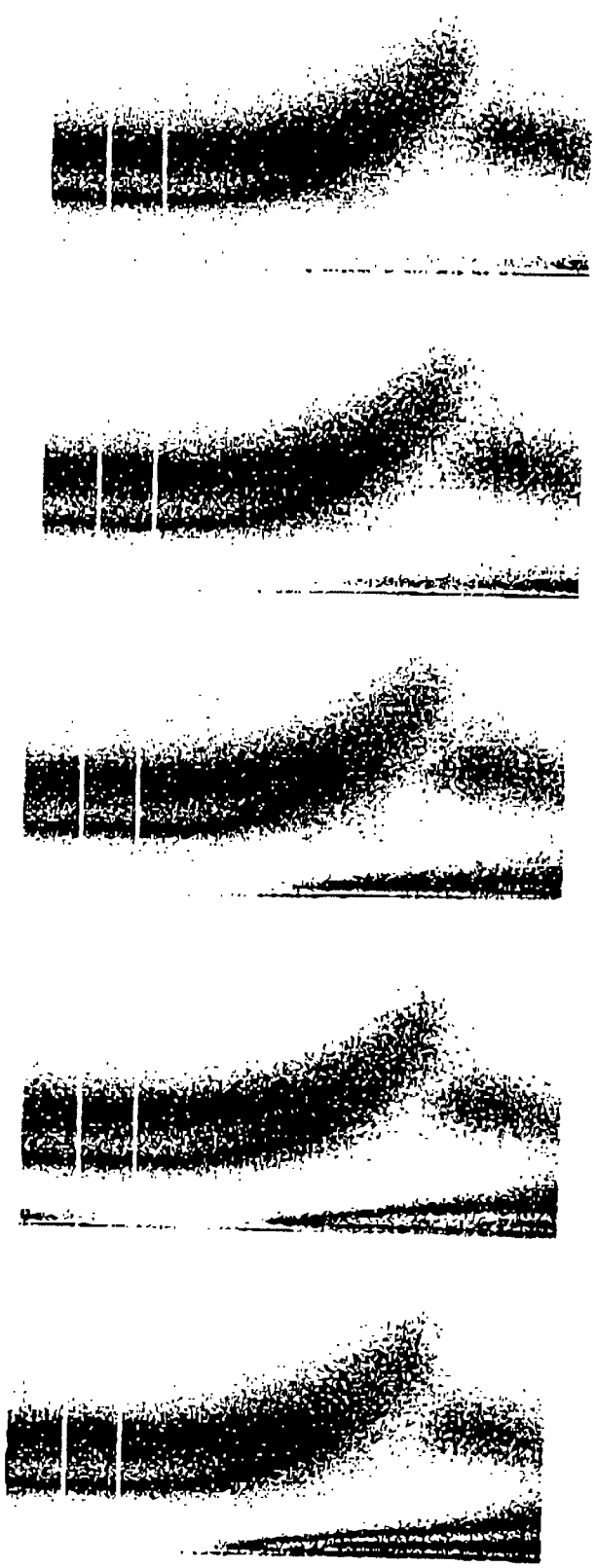
Figure 5:
Figure 5:
Figure 5:
Figure 5:

FIG. 1 is a blood sample from a healthy person. As the stress is increased from point A onwards, the cells begin to swell resulting in the gradual increase in mean cell size. At a certain osmolality the cell size can increase no more, and upon a further increase-in stress, the cells evacuate their contents to become "ghost cells" as shown at region B. These characteristics of cells yield diagnostic information which is useful alongside the techniques of the present invention. However, the present invention is unconcerned with these characteristics and is independent of them, but is instead concerned with the cells which appear along the baseline of the graph of FIG. 1. The nature of these small baseline cells can be differentiated by their distribution against osmotic stress, their distribution against mechanical stress and/or their response to contact with air. Platelets are uninfluenced by osmotic stress within the range tested (300–100 mOsm/Kg). However, fragments are strongly influenced by osmotic stress. They rarely appear without the provocation of lysis and become more numerous as lysis increases. Thus fragments vary inversely with osmolality. Mechanical stress has opposing effects on platelets and fragments, an influence that is intensified by concomitant exposure to air. It provokes the appearance of fragments but it induces the lysis of platelets rendering them invisible.

FIGS. 2A–F demonstrate that platelets are rendered invisible with progressive agitation in air (with respective agitation periods of 0, 1, 2, 6, 10 and 15 seconds). The signal along the base line in FIG. 2A is attributable to the presence of platelets since their frequency is approximately the same at all osmolalites, and since even 2 seconds of agitation in air induces almost complete disappearance (see FIG. 2C). The phenomenon cannot be attributed to platelet attachment to the red cells or white cells (satelitism) since FIGS. 3A–F shows the same phenomenon in a pure platelet suspension when no other cells types are present.

FIGS. 4A–E demonstrate the effect of mechanical agitation in air with time. As the agitation period proceeds going from 4A down to 4E the number of fragments generated increases. At the same time, platelets are rapidly made invisible (although it is difficult to see this in these particular figures). FIGS. 5A–D demonstrate the platelet reduction in a whole blood sample on shaking with air. Such frequency distributions have previously been used, for example, in WO 97/24598, WO 97/24599, WO 97/24601.

The preferred method comprises measuring platelets, using existing automated particle counters, mixing and testing the sample in the absence of air. If some air is unavoidable, the surface area of the samples meniscus should be minimized to limit the effect on the sample or alternatively a gas which has no effect on the platelets should be used. This single measurement will provide an accurate count for all samples which do not contain particles of a similar size to the platelets. Repeat measurements are taken after controlled agitation with air to render the platelets invisible to an automated analyser. The difference between the population from the two measurements provides a measure of the number of platelets, their age and physiological properties. In a whole blood sample, only the platelets will disappear. For instance, if the cell counts before and after agitation with air do not differ, then there are no platelets in the suspension.

We have measured platelets under a variety of experimental conditions: in pure platelet suspensions, in the presence of all other blood cell elements, in containers of glass, polystyrene and polypropylene, after exposure to varying surface areas in a thin film and by shaking with varying quantities of glass beads, after exposure to varying osmotic, mechanical, thermal, and sonic stress, and after mechanical agitation with air and nitrogen.

By measuring the platelet count against all these stresses, we have found conditions which render platelets electronically invisible, while other types of cells are unaltered or transformed but remain visible to automated analysers. Moreover the speed and characteristic of the disappearance is an indication of platelet health and function.

In all laboratories, prior to any analysis on any blood sample, the sample is first shaken to mix the cell types randomly with respect to each other and with the plasma. The agitation is continued during the process of analysis in automated instruments, and the cells are exposed to agitation in the presence of a variable amount of air, both deliberately and accidentally. Indeed, many instruments use air bubbles as a way to separate each bolus of blood or clean the tubes and instrument conduits.

Shaking with glass beads has a small effect on the platelet count and may therefore be preferable to shaking with air or some other gas for initial sample mixing when the aim is to avoid platelet disappearance. The mechanical effect of shaking was further differentiated from the effect of air admixture by continuously withdrawing aliquots from a conical flask when it contained no air (being full of the blood suspension) until it was empty containing nothing but air. All the while the blood suspension was continuously agitated with a stirring bar. The platelet count remained constant so long as the flask was full, but once the sample/air ratio fell below a half, the platelets began to disappear and did so in direct proportion to the volume of air in the flask. In the absence of air, the platelets do not disappear appreciably within seconds as they do in the presence of air. Thus counting the platelets against duration or intensity of agitation with air (or its components), will induce them to diminish or completely disappear but bacteria, fragments or any other element that may be found in the blood with neither diminish nor disappear.

The method is useful in the following:
1. IMPROVED DISEASE DIAGNOSIS. More accurate platelet counts will lead to better disease diagnosis and prognosis.
2. EXISTING METHODS OF BLOOD TESTING. By using an inert gas, or eliminating air from the mixing, automated instruments will improve the accuracy and repeatability of platelet counting and sizing.
3. A NEW MEASURE OF PLATELET HEALTH. By using this method, new information about platelet health is derived from their sensitivity to air and their rate of disappearance and reappearance.
4. BLOOD COLLECTION. Currently Vacutainers (trade mark) (partial vacuum glass specimen tube) contain air, and more is sometimes admitted when the sample is smaller than required.

What is claimed is:

1. A method of determining a measure of the number of platelets in a cell suspension containing platelets, the method comprising the steps of:
    counting the number of small particles in the suspension;
    agitating the suspension in the presence of a gas;
    counting the number of small particles in the suspension after agitation; and,
    comparing the two counts to obtain a measure of the number of platelets.

2. A method according to claim 1, in which the gas is air, or one or more of its constituent gases.

3. A method according to claim 1, in which one or more aliquots of the suspension are passed through a particle counter before the suspension is agitated to obtain a first count of the number of small particles and subsequently one or more other aliquots of the suspension are passed through a particle counter after agitation to obtain a second count of the number of small particles in the sample.

4. A method according to claim 1, in which the cell suspension is isotonic.

5. A method according to claim 1, in which small particles having a volume of at least 7 femtoliters are detected to obtain a count of the number of small particles in the suspension.

6. A method according to claim 1, in which the suspension is subjected to a series of alterations in osmolality and a count of the number of small particles in the suspension obtained at a number of different osmolalities.

7. A method according to claim 1, in which at least one of the air quantity in contact with the suspension, the intensity of agitation, and the duration of agitation, is measured.

* * * * *